United States Patent [19]

Fatula, Jr.

[11] Patent Number: 4,529,230
[45] Date of Patent: Jul. 16, 1985

[54] CAPILLARY TUBING AND SMALL ROD CONNECTOR

[76] Inventor: William F. Fatula, Jr., P.O. Box 350, Bellefonte, Pa. 16823

[21] Appl. No.: 352,868

[22] Filed: Feb. 26, 1982

[51] Int. Cl.³ .............................................. F16L 17/02
[52] U.S. Cl. .................... 285/341; 285/343; 285/353; 285/369; 285/DIG. 12
[58] Field of Search .............. 285/177, 343, 369, 353, 285/DIG. 12, 423, 341, 342, 348

[56] References Cited

U.S. PATENT DOCUMENTS

| | | | |
|---|---|---|---|
| 822,530 | 6/1906 | Lowe | 285/353 X |
| 823,944 | 6/1906 | Hart | 285/353 X |
| 2,287,142 | 6/1942 | Simmonds | 285/353 X |
| 2,755,110 | 7/1956 | Jacobs | 285/423 X |
| 3,880,452 | 4/1975 | Fields | 285/177 |
| 4,035,168 | 7/1977 | Jennings . | |
| 4,076,286 | 2/1978 | Spontelli . | |
| 4,116,837 | 9/1978 | Biermacher . | |
| 4,173,363 | 11/1979 | Stearns | 285/177 |
| 4,291,903 | 9/1981 | Fields | 285/177 X |

FOREIGN PATENT DOCUMENTS 2729359 1/1978 Fed. Rep. of Germany ...... 285/177
3045654 12/1980 Fed. Rep. of Germany .

OTHER PUBLICATIONS

Unit Construction System for Coupling Operations in High Resolution Gas Chromatography; Werner Dosch, pp. 549–561.

*Primary Examiner*—Dave W. Arola

[57] ABSTRACT

A connector for the joining together two fused silica or glass or other types of capillary tubes, in a chromatography system, without detrimental chromatographic effects created by distortion of the two joined capillary tubes, dead volumes or exposure to metal surfaces, or for the butt joining of glass rods, has a pliable elongate surrounding member which sealingly engages a substantial length of each tube or rod from its end as well as supports each and thereby eliminates exposure to a housing or container surface.

10 Claims, 6 Drawing Figures

U.S. Patent   Jul. 16, 1985   4,529,230
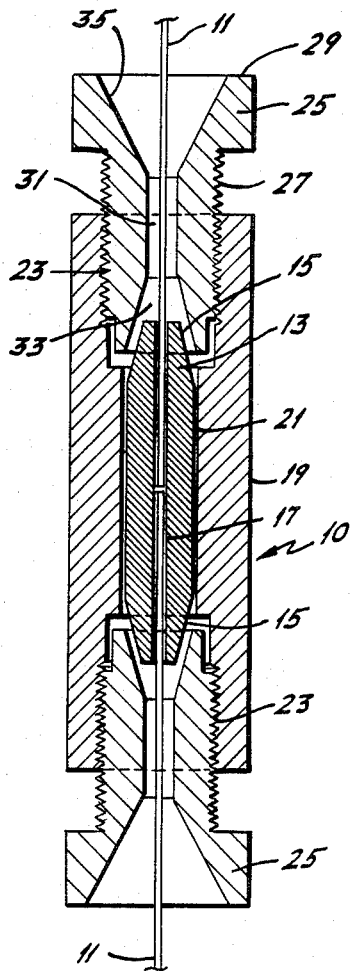
FIG. 1.
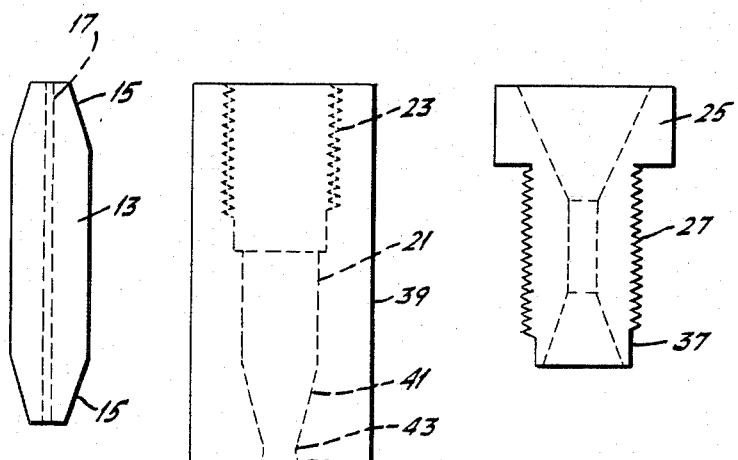
FIG. 2.   FIG. 4.   FIG. 3.
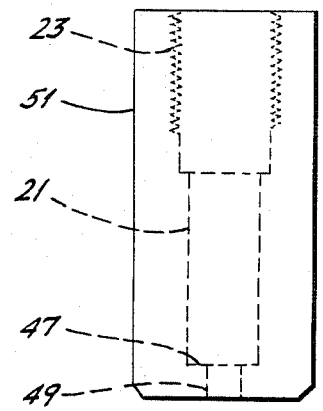
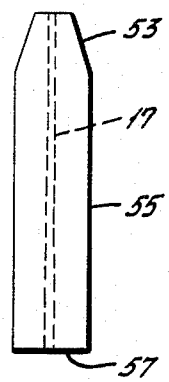
FIG. 5.   FIG. 6.

CAPILLARY TUBING AND SMALL ROD CONNECTOR

BACKGROUND OF THE INVENTION

This invention relates in general to tubing connectors and rod connectors and in particular to connectors for joining capillary tubes of the type used in gas chromatography equipment and other highly sensitive scientific measuring devices or for joining fiber optic rods.

Tubing couplings or tubing fittings in the past have taken variations of two basic forms of pressure fit, these being created by (1) a compressed ring or (2) a physical distortion of the end of the tubing. In the first instance, an o-ring or compression ring is wedged between mating surfaces of a coupling housing comprising the fitting. As a matter of course, two rather substantially constructed members, one acting as a housing and the other acting as a cap are drawn together. Each of these members can have a tapered surface or equivalent structure which bears down upon the ring deforming it and creating a pressure by the ring against the outside diameter of the tubing. This creates a pressure seal between the coupling members and the tubing. The deformable ring occupies a very short distance along the outer diameter of the tubing so that when it is deformed it concentrates specific pressure forces at a very narrow region of the tubing to create the seal. These forces very often permanently deform the wall of the tubing or at least distort it which effects the flow characteristics through the tubing at that point.

In the second instance of the distortion of the tubing, the end of the tubing is flared for mating with the outside taper of a tapered fitting and for being compressed thereagainst by a cap having a similar tapered surface and which threadably engages its mated coupling part. The flaring of this tubing and the insertion of the flared end into the mating tapered surface creates a protrusion into the tubing passageway which effects the flow characteristics through that section.

With large I.D. tubes the effects are minimal, but with capillary tubes these flow characteristic effects can be very significant. Moreover, with these types of couplings two compression members must be used and the fluid flowing through the coupling comes in contact with metal or other surfaces of the coupling housing.

Spontelli, U.S. Pat. No. 4,076,286, provides a tubing fitting wherein a coupling body 12 has a square shoulder against which the end of the tubing seats to create a smooth continuation for the interior wall or passageway. An annular ring 50 has a convex outer surface 56 which seats against and is drawn up to a tapered shoulder 28 of the coupling body 12 when a coupling nut 34 is drawn upon the coupling body 12 by means of threads 30. This causes a crushing of the annular ring 52 to press and impinge on the outer wall of the tubing. As shown in FIG. 2 of the patent, the wall of the tubing is typically distorted at the pressure points to create the positive seal needed.

Jennings, U.S. Pat. No. 4,035,168, provides an inlet splitter for gas chromatograph. This structure includes a coupling structure for mating to a capillary tube 16. This structure includes an end closure 102 having a bore therethrough and an annular fitting into which an aperture nut 106 mounts. The aperture nut carries a central bore through which the capillary tube 16 passes. A sealing means 108 identical to sealing member 70 is caused to spread and thereby clamp down about the capillary tubing 16 as the aperture nut 106 is screwed into the end closure 102. This sealing member can be constructed of rubber, neoprene or silicon and causes a pinching at a narrow area of the capillary tubing wall to create a seal.

Biermacher, U.S. Pat. No. 4,116,837, provides an in line filter arrangement for a hard pressure liquid chromatography apparatus including couplings for mating two stainless steel capillary tubings. A SWAGELOK (trademark) fitting is used for coupling two one-sixteenth inch stainless steel capillary tubing 14. Tube 14 is provided with a fitting member or cap which is threadably engaged onto the external threads of a nipple 12. Each SWAGELOK fitting includes a sealing member which is distorted by the fitting member as it is tightened down on the nipple, causing it to press with great force at a specific point along the capillary tubing.

The construction and connection of capillary tubing is critical in many applications where used in sensitive measuring devices, and none is more critical than in gas chromatographic equipment. The physical structure of the tubing must be maintained constant throughout so that the dynamic characteristics of the fluid passing therethrough are not drastically effected from turbulation, back pressures, dead spaces or other factors. Often inert material, such as fused silica or glass, is used for capillary tubes on chromatograph equipment. The joining of two such silica or glass tubes, or when used, metal capillary tubing, without detectable detrimental chromatographic effects has been a problem.

The prior art often uses two sealing rings to connect the ends of the capillary columns or tubes within a housing device. This metal housing serves as a splice while introducing both dead volume and flow disruption. It is desirable to provide a capillary tubing coupling which minimizes dead volume, flow disruption and eliminates fluid exposure to coupling housing surfaces.

Moreover, each of these prior art coupling structures provides a coupling seal by pressure forces exerted between the mating surfaces of three elements: the tubing and the seal member on one hand, and the seal member and the housing on the other hand.

An object of the present invention is to provide a capillary butt connector for joining the ends of two capillary tubes in close proximity to one another and for minimizing dead volume between the joined ends thereby minimizing chromatographic analytical readout inaccuracies.

A second object of this invention is to provide such a butt connector where the tubes joined are surrounded by a sealing and support structure which is pliable and extends a sufficient distance from the joined ends.

A further object is to provide such a connector where the sealing member reacts to longitudinal forces on it to expand laterally thereby providing a coupling seal between the seal member and tubes alone and thereby eliminating the absorptive effects of fluid contact with the connector housing.

SUMMARY OF THE INVENTION

The objects of this invention are realized in a coupling device for capillary tubing such as fused silica or glass capillary tubes or for coupling other types of fine rods such as butt joining fiber optic rods. A double ended tapered ferrule may be incorporated as the principal connection and sealing structure. This ferrule may be of pliable, plastic-like material and be cylindrically shaped with a tapered portion at each end. It may include a longitudinal hole or bore along its center line. The ferrule may be inserted within a cylindrical sleeve carrying internal end threads. An apertured nut, which allows a capillary tube to pass therethrough, is threadedly inserted into the sleeve with a beveled mating surface to bear against the ferrule.

Capillary tubes or fiber optic rods to be joined are inserted into the ferrule bore to abut one another at approximately the midpoint of the ferrule, the bore being of a size to permit a neat fit with the tubes and align the ends with one another. The ferrule is of sufficient length to extend a substantial distance from the end of each tube to provide mechanical support thereto, and is pliable enough to allow for slight irregularities in the tubes. Upon tightening down of the apertured nut, the ferrule is deformed longitudinally and expands laterally in its mid-area while being compressed laterally at each end, to bear against the sleeve and against the portions of each tube or rod inserted therein providing a seal between the abutted tubes or rods and the ferrule.

The bore within the ferrule can be customized to splice any of the available sizes of capillary tubing by enlarging the bore size to approximately the outside diameter of the tubing. The bore can also be enlarged on one side only to join tubes or rods of dissimilar outside diameters.

The sleeve may be constructed with an internal shoulder at one end against which one end of the ferrule abuts necessitating but one apertured nut for deforming the ferrule and compressing it into a sealing state. The sleeve may also be constructed as a cylinder, open at both ends with internal threads at both ends. Two apertured nuts are utilized with this latter configuration.

DESCRIPTION OF THE DRAWINGS

The advantages, structural features and operation of the invention can easily be understood from a reading of the following detailed description of the invention in conjunction with the attached drawings in which like numerals refer to like elements and in which:

FIG. 1 shows a cross sectional view of the assembled capillary tubing connector with which two tubing sections have been connected;

FIG. 2 shows the double ended ferrule of the embodiment of FIG. 1;

FIG. 3 shows the apertured nut for the connector of FIG. 1;

FIG. 4 shows an alternate sleeve for the tubing connector wherein a single apertured nut of FIG. 3 and a single double ended ferrule of FIG. 2 are used;

FIG. 5 shows a further embodiment for the sleeve for the connector having a square shoulder at one interior end thereof;

FIG. 6 shows a single tapered end ferrule for use with the sleeve embodiment of FIG. 5.

DETAILED DESCRIPTION OF THE INVENTION

A connector device 10 is used for the connection of capillary tubes 11, or alternately the butt connection of fiber optic rods, to provide a sealed coupling of the tubes 11 without detectable detrimental chromatographic effects such as excessive dead volume or flow disruption caused by turbulence or other irregular flow characteristics created by another type of coupling. An elongate pliable cylindrical ferrule 13 has each end 15 thereof tapered as a trunkated cone or conical frustrum 15. This ferrule 13 has a central bore 17 extending along its longitudinal axis into which the two capillary tubes 11 are inserted in a neat fit to abut one another, the ferrule 13 acting as the sole splicing member for joining and sealing the ends of the two capillary tubes 11.

The ferrule 13 is positioned within a cylindrically shaped housing 19 in a smaller diameter bore midsection 21. Both ends of the cylindrical sleeve 19 are enlarged and threaded with threads 23 extending inwardly from the end faces of the cylindrical sleeve 19.

A cap or apertured nut 25 is threaded on its shaft 27 and has a hexagonally shaped head 29 and is fitted on each threaded end 23 of the sleeve 19. Each apertured nut 25 has a center bore 31 with a tapered or bevel portion 33, 35 at either end, the first tapered or bevel portion 33 being on the end of the shaft of the nut 25 which seats against the ferrule 13.

Cylindrical sleeve 19 can be made out of stainless steel, such as No. 304 stainless, and forms the housing for the connector 10. This sleeve 19 need not have a cylindrical outer wall, but can be hexagonal shaped or otherwise, and can be made of other metals or hard materials such as brass.

When chromatographic capillary tubing, made of fused silica or laboratory glass material of a size in the range from 0.33 mm to 1.58 mm outside diameter is to be connected, the sleeve 19 has an outside diameter of about ¼ inch and is about 1 inch long. The small bore section 21 of the sleeve 19 is about ⅜ inch long and has an inside diameter of about ⅛ inch. The larger diameter bore section at either end of the sleeve are each about 5/16 inch long with a threaded section 23 extending inwardly from each end about ¼ inch.

Each apertured end cap 25 is also made of No. 304 stainless steel or other hard material and is about ½ inch long. The hexagonal head 29 is about ¼ inch and the threaded portion that extends is about 5/16 inch long and cut to 10–32 American standard fine thread specifications. The center bore of each cap 25 has an inside diameter of about 1/16 inch and is about 3/16 inch long. The first tapered portion 33 tapers at an angle of about 25° and starts with an outside diameter of about 0.128 inches. The second tapered portion 35 has an outside diameter of about 0.218 inches and tapers at an angle of about 35°.

The double ended ferrule 13 is about ½ inch long and is made of E. I. duPont SP-1 Polymide Vespel (trademark). This material is a pliable, plastic-like material which is slightly deformable. The outside diameter of the ferrule 13 is approximately ⅛ inch with each of the conical frustrum ends 15 tapering at an angle of about 15°. The center cylindrical section of the ferrule 13 is about 5/16 inch long with the truncated end diameter of the frustrum ends 15 being each about 0.075 inches.

The ferrule 13 can also be made of silicone rubber, Teflon*, Kelrez*, graphite or similar materials.
*Trademarks of E. I. duPont The ferrule 13, FIG. 2, has a center bore of about 0.0145 inches which can be enlarged when larger outside diameter capillary tubing is to be connected.

Extending beyond the threaded portion 27 of the apertured nut 25 is a slightly undersized shaft portion 37, FIG. 3. This shaft portion 37 extends about 1/16 inch beyond of the threads 27 to provide the first beveled portion 33 of the nut 25 with a taper of about ⅛ inch long.

The connector 10 is easily assembled by first inserting one of the capillary tubes 11 into one end of the ferrule 13 with one of the apertured nuts 25 already inserted over the capillary tubing 11. The ferrule 13 is then inserted into the center portion of the sleeve 19 while that particular first one of the apertured nuts 25 is threaded onto an end of the sleeve 19. The second of the capillary tubes 11 is then inserted into the ferrule 13 bore 17 from the other end with its respective apertured nut 25 already asserted over the capillary tubing 11. Both apertured nuts 25 are then tightened down so that their first tapered portions 33 bear against the respective tapered end portions 15 of the ferrule 13 causing the ferrule 13 to be compressed longitudinally deforming it slightly and causing it to expand laterally against the inside walls of the sleeve 19 and the tubes 11 which creates a pressure along the entire length of the ferrule 13 between the ferrule 13 and the capillary tubing 11 thereby providing a seal and engagingly supporting the two capillary tubes 11 in a butted position. No portion of the connector sleeve 19 (housing) or nuts 25 forms an interface of the seal.

As an alternate to the embodiment of FIG. 1, the housing comprising the sleeve 19 may be made in an alternate configuration necessitating but one apertured nut 25, FIG. 4. This alternate configuration would have the cylindrical sleeve 39, FIG. 4, with an identical inside diameter center bore portion 21 and a single threaded portion 23 at one end of the cylinder 39. The center bore portion 21, however, would conically taper inwardly at an angle of about 25° at the end opposite from the threaded section 23. This conical taper section 41 would be about ⅛ inch long and would end in an inside diameter 43 of about 1/16 inch which would then continue as a taper bore 45 flaring outwardly at an angle of about 35°. These sections 41, 43, 45 of the housing 39 would perform an identical function as the second one of the apertured nuts 25 and would eliminate the necessity for a second one of these nuts 25. With this alternate embodiment, FIG. 4, as the single apertured nut 25 is drawn in on the threads 23 the ferrule 13 which has been inserted within the sleeve 39 is compressed longitudinally which causes it to expand laterally and press against the outside walls of both capillary tubes 11 which have been inserted from either end of the ferrule 13 bore 17.

The housing may be further modified to be sleeve 51, FIG. 5, to have the interior end of the midsection bore 21 truncate in a square shoulder 47 which extends perpendicular to the longitudinal axis of the sleeve 51. A center bore of about 1/16 inch 49 extends from the shoulder 47 the remaining distance through the sleeve 51. The double ended ferrule 13 of FIG. 2 used in the embodiment of FIG. 1 and embodiment of FIG. 4 would be modified for use with this latter sleeve housing 51. In this latter instance there would be but a single tapered end 53 on the ferrule 55 with the opposite end of this modified ferrule 55 being squared off 57. This ferrule 55 would be inserted through the threaded end 23 of this sleeve 51 before either of the pair of capillary tubes 11 would be inserted into the bore 17 of this ferrule 55. This ferrule 55 would be made of similar or identical materials to the ferrule 13.

The inside dimensions of the nut 25 apertures 31, 33, 35, sleeve 39 apertures 41, 43, 45 and sleeve 55 aperture 49 are such as to leave sufficient clearance for the tubes 11 whereby the ferrules 13 or 55 provide the entire supporting surface for the tubes 11 and a slight movement or bend of the tubes 11 is tolerated without a touching of the walls of the nut 25 or sleeves 39, 51.

Many changes in the above described coupling can be made without departing from the intent and scope of the invention. It is understood that the coupling 10 is similarly useful in joining fiber optic rods and other small cylindrical members and that these are understood to be included in any discussions of the tubes 11 hereinabove. It is intended, therefore, that all matter contained in the above description and shown in the accompanying drawings be interpreted as illustrative and not be taken in the limiting sense.

What is claimed is:

1. A connector to join together in aligned abutment the free ends of each of two capillary tubes, comprising:
   a single piece sealing means having opposite ends and having a single bore for receiving said two capillary tubes free ends in axial abutting alignment, said sealing means having the wall at each end thereof extending about said bore and tapering at a shallow angle less than 30° to a smaller dimension;
   a housing for surrounding and containing said sealing means, said housing being spaced about and away from the intended position of said joined two capillary tubes received within said sealing means; and
   a pair of end caps, each having engaging means, each engaging by said means a respective end of said housing through which a said capillary tube is intened to extend, each said end cap having a first tapered surface intened to engage a said tapering wall of said sealing means thereby exerting pressure thereagainst causing said sealing means to deform against said housing and said tube ends, said each end cap having a central bore being larger in diameter than said capillary tube end diameters for spacing from said intended capillary tube, said bore flaring to a second taper at the end opposite said first tapered surface, said second taper forming an enlarged cavity enabling accentuated movement of a said capillary tube extending about therethrough about without contact with said end cap.

2. The connector of claim 1 wherein said single piece sealing means is an elongate plastic cylinder having each end tapered in a conical frustrum shape with said bore extending along the longitudinal axis through said cylinder and said frustrum ends; and wherein each said end cap comprises an externally threaded cylinder portion at one end having a center longitudinal bore and a wrenching surface portion at the opposite end thereof, said end cap center bore flaring to larger diameters at each end thereof, the flared bore at said one end forming said first tapered surface and providing a first conical surface matable directly to a conical frustrum end of said elongate cylinder and the flared bore at said opposite end providing a second conical surface forming said enlarged cavity.

3. The connector of claim 2 wherein said housing is a cylindrical sleeve having a smaller diameter center bore and larger diameter bores at either end thereof, said larger diameter and bores each having a threaded portion extending from the outside end thereof; and a said end cap engaging means includes threads threadedly engaging each said end bore threaded portion.

4. The connector of claim 3 wherein said elongate plastic cylinder is a cylindrical double tapered ended ferrule, having a uniform center bore which is approximately ¼ to 1 times the outside diameter of said two capillary tubes, said ferrule tapered ends each tapering at an angle of 15° forming a said conical frustrum end.

5. The connector of claim 4 wherein said cylindrical sleeve is about 1 inch long, said sleeve smaller diameter center bore is about ⅜ inches long, said sleeve larger diameter end bores are each about 5/16 inches long with said threaded portion is about ¼ inches long; wherein said ferrule bore is about 0.0145 inches in diameter, said ferrule center cylindrical portion is about 5/16 inches long and said ferrule conical frustum ends are each about 0.075 inches long; and wherein each said end cap wrenching surface portion is a hexagonal head and said threaded portion bore is about 1/16 inch diameter, said one end bore flare is at an angle of about 25° to about a 0.128 inch inside diameter, and said opposite end bore flare is at an angle of about 35° to about a 0.218 inch inside diameter.

6. The connector of claim 5 wherein said ferrule is of plastic-like-type material.

7. A connector to join together in aligned abutment the free ends of each of two capillary tubes, comprising:
   an elongated cylindrical ferrule having a center portion, tapered conical ends at each end thereof tapering inwardly at an angle less than 30° to a smaller outside diameter, and a longitudinal axial bore extending through said center portion and each said bore intended to receive said two capillary tubes;
   a sleeve for surrounding and containing said ferrule having a central bore portion, a conically inwardly tapering bore portion extending from one end of said central bore portion and cylindrical threaded bore portion extending from the other end of said central bore portion; said sleeve being spaced about and away from the intended position of said joined two capillary tube ends received within said ferrule and
   a threaded end cap engaging said sleeve threaded bore, said end cap having a central bore with outwardly flared tapers at each end thereof; wherein when said ferrule is positioned within said sleeve, said end cap engages the free end of said ferrule as said cap is screwably drawn into said sleeve, thereby exerting pressure against said ferrule to deform said ferrule against said sleeve and tube ends and wherein said end cap central bore and the minimum bore of the conically inwardly tapering portion are larger in diameter than the diameter of the capillary tube ends for spacing about and away from the intended position of said two capillary tubes and said outwardly flared tapers on said end cap forming cavities on each end thereof, the cavity opposite the one adjacent the ferrule being sized to enable accentuated movement of the capillary tube extending therethrough without contact with said end cap.

8. The connector of claim 7 wherein said conically inwardly tapering bore portion of said sleeve tapers at an angle of about 25° to a reduced inside diameter then flares outwardly at an angle of about 35° to a larger inside diameter, and wherein said cylindrical ferrule tapered conical ends each taper inwardly to a reduced diameter at an angle of about 15°.

9. The connector of claim 8 wherein said sleeve inwardly tapering bore portion is about ⅛ inches long, said reduced inside diameter which said bore tapers to is about 1/16 inches.

10. A connector to join together in aligned abutment the free ends of each of two capillary tubes, comprising:
   An elongated cylindrical ferrule having a center portion, a first tapered end tapering inwardly at an angle less than 30°, to a smaller outside diameter an opposite squared-off end and a longitudinal bore extending entirely therethrough; said bore being sized to receive the abutting ends of the two capillary tubes;
   a sleeve for surrounding and containing said ferrule a central bore portion, a reduced bore portion extending at one end from said central bore and forming a shoulder against which said squared-off end of said ferrule can seat and an enlarged threaded bore portion extending at the other end from said central bore; said sleeve being spaced about and away from the intended position of said two joined capillary tubes received within said ferrule and
   a threaded end cap for engaging said threaded bore portion of said sleeve thereby drawing against said ferrule to deform said ferrule against said sleeve and tubes;
   wherein said end cap has a central bore which tapers outwardly at both ends, thereby forming cavities at each end thereof; said central bore of said end cap and said reduced bore portion of said sleeve each having a diameter larger than the diameter of the capillary tube ends so as to be spaced therefrom, the first end taper thereof engaging said ferrule tapered end, said cavity in said end cap opposite said first taper being sized to enable accentuated movement of said capillary tube extending therethrough without contact with said end cap.

* * * * *

UNITED STATES PATENT AND TRADEMARK OFFICE
CERTIFICATE OF CORRECTION

PATENT NO. : 4,529,230
DATED : July 16, 1985
INVENTOR(S) : William F. Fatula, Jr.

It is certified that error appears in the above-identified patent and that said Letters Patent is hereby corrected as shown below:

Title page:

Assignee: Supelco, Inc.
Supelco Park
Bellefonte, Pennsylvania 16823

Column 6, line 41: delete "about"

Column 6, line 42: delete "about"

Column 8, line 27: after "ferrule" insert --having--

Signed and Sealed this

Twenty-first Day of October, 1986

[SEAL]

Attest:

DONALD J. QUIGG

Attesting Officer

Commissioner of Patents and Trademarks